United States Patent [19]

Schäfer et al.

[11] Patent Number: 5,346,818

[45] Date of Patent: Sep. 13, 1994

[54] **METHOD FOR THE CONJUGATIVE TRANSFER OF MOBILIZABLE VECTORS FOR *E. COLI* TO GRAM-POSITIVE BACTERIA AND VECTORS SUITABLE FOR USE IN SUCH A METHOD**

[75] Inventors: Andreas Schäfer; Jörn Kalinowski; Alfred Pühler, all of Bielefeld, Fed. Rep. of Germany

[73] Assignee: Degussa Aktiengesellschaft, Frankfurt am Main, Fed. Rep. of Germany

[21] Appl. No.: 447,139

[22] Filed: Dec. 8, 1989

[30] Foreign Application Priority Data

Dec. 9, 1988 [DE] Fed. Rep. of Germany ....... 3841453

[51] Int. Cl.$^5$ ............... C12N 15/00; C12N 15/63; C12N 15/74; C12N 15/77
[52] U.S. Cl. ............... 435/172.3; 435/252.3; 435/320.1; 536/24.1; 935/29; 935/56
[58] Field of Search ........... 435/172.3, 252.2, 252.33, 435/69.8, 69.1, 320.1, 172.1, 843, 252.3; 935/27, 29, 86; 536/24.1

[56] References Cited

PUBLICATIONS

Haima P. et al., *Mol. Gen. Genet.* 209:335–342 (1987).
Product Catalogue, Bethesda Research Laboratories, pp. 88–92 1988.
Simon, R., et al. *Methods in Enzymology* 118:640–659.
Trieu–Cuot, P., et al. *FEMS Microbiology Letters* 48:289–294 (1987).

*Primary Examiner*—Robert A. Wax
*Assistant Examiner*—Dian C. Jacobson
*Attorney, Agent, or Firm*—Cushman, Darby & Cushman

[57] ABSTRACT

The present invention relates to a method of effecting the conjugative transfer of a mobilizable vector from cells of an *E. coli* mobilizer strain to gram-positive bacterial cells. The invention also relates to vectors suitable for use in such a method.

20 Claims, 6 Drawing Sheets

METHOD FOR THE CONJUGATIVE TRANSFER OF MOBILIZABLE VECTORS FOR E. COLI TO GRAM-POSITIVE BACTERIA AND VECTORS SUITABLE FOR USE IN SUCH A METHOD

BACKGROUND OF THE INVENTION

1. Technical Field

The invention relates to a method for effecting the conjugative transfer of mobilizable vectors from *E. coli* into gram-positive bacteria and to vectors suited for this purpose.

2. Background Information

The use of transposons for mutagenesis, gene isolation and gene analysis was, in the past, largely limited to gram-negative bacteria. The mutagenesis of *Bacillus subtilis* by the transposon Tn917 can be considered an exception in this connection (Youngman et al., PNAS USA 80, 4 (1983), pp. 2305–2309) which is made possible by the fact that *B. subtilis* has a natural competence for taking up plasmid DNA from the surrounding medium.

P. Trieu-Cuot et al. (FEMS Microbiology Letters 48 (1987), pp. 289–294) describe the plasmid transfer from *E. coli* into certain gram-positive bacteria by means of conjugation; only very unsatisfactory values are achieved, however, with transfer frequencies of $10^{-7}$ to $10^{-8}$. In addition, Applicants' own tests show that a transfer into *Corynebacterium glutamicum* cannot be demonstrated with the system described therein.

U.S. Pat. Nos. 4,626,506, 4,680,264 and 4,686,184 (Puhler et al.) and Simon et al. (Biotechnology, November, 1983 and Methods in Enzymology, vol. 118, pp. 640–659) teach the mutagenesis of gram-negative bacteria using mobilizable *E. coli* vectors. In contrast, the present invention provides a method for effecting the conjugative transfer of mobilizable vectors from *E. coli* to gram-positive bacteria and vectors suitable for use in same.

SUMMARY OF THE INVENTION

The invention is directed to providing a solution to the problem of developing a conjugative transfer protocol according to which mobilizable vector plasmids can be transferred, in high frequency, from *E. coli* to gram-positive, especially Coryneform, bacteria.

Further objects and advantages of the present invention will be clear to one skilled in the art from the description of the invention that follows.

BRIEF DESCRIPTION OF THE FIGURES

FIG. 1: The vectors pCV35, pSUP102 and pECM1.
Legend:
kan: DNA sequence which imparts resistance to the antibiotic kanamycin
cm: DNA sequence which imparts resistance to the antibiotic chloramphenicol
tet: DNA sequence which imparts resistance to the antibiotic tetracycline
ori V: Starting point of the vegetative replication in *E. coli*
ori T: Starting point of the transfer replication
FIG. 2: The mobilizable *E. coli—C. glutamicum* shuttle vector pECM3.
Legend:
ori V: Starting point of the vegetative replication in *E. coli*
ori T: Starting point of the transfer replication, part of the "mob" site
cm: DNA sequence which imparts resistance to the antibiotic chloramphenicol The pHM1519 portion of vector pECM3 extends from nucleotide 2200 to nucleotide 5100.

FIG. 3: Mutation of chromosomal DNA by gene disruption.
Legend:
$Cm^R$: chloramphenicol acetyltransferase gene
$Km^R$: aminoglycoside phosphotransferase gene
lysA: lysA gene coding for mesodiaminopimelate-dehydrogenase
lysA-int: internal fragment of the lysA gene lacking start and stop of the coding region
$\Delta$lysA: incomplete genes after integration of pEMlys2 which are missing either beginning or end of the coding region FIG. 4: Construction of the vector pK18 l ys.
Legend:
km: kanamycin resistance gene
lacZ-alpha: N-terminal region of the lacz gene
lysA: lysA gene
lysA-int: internal fragment of lysA gene
oriV: starting point of vegetative replication in *E. coli*

DETAILED DESCRIPTION OF THE INVENTION

The present invention is directed to a method for effecting the conjugative transfer of mobilizable vectors from *E. coli* to gram-positive bacteria wherein restriction-defective cells of gram-positive bacteria are produced and are crossed, according to known methods, with an *E. coli* mobilizer strain carrying the mobilizable vector. While the donor is preferably in the logarithmic growth phase, the stationary growth phase has proven to be the advantageous state of the recipient. Donor and recipient cells are generally used in a ratio of 1:2 to 1:10, preferably 1:4 to 1:6, especially 1:5.

Suitable mobilizable *E. coli* vectors are not self-transferrable. The concept of *E. coli* vectors comprises, in general, all plasmids which replicate independently only in *E. coli* strains and which are recognized in the art as being useful in genetic engineering applications. Examples of such *E. coli* vectors include pMB9, pBR322, pBR325, pKB111, pUC8, pUC9, pACYC184, pACYC177, and pSC101. Typical *E. coli* vectors such as pBR325 (Bolivar, F. et al., Gene 2, p. 95, (1977)) or pACYC184 (Chang, AC. Y. and Cohen, S. N., J. Bact. 134, p. 1141 (1978)) are neither self-transferrable nor sufficiently mobilizable. These and other vectors which replicate only in bacterial strains of the *E. coli* group are modified by insertion of the "mob" site of a plasmid with a broad host range into gram-negative bacteria. The plasmid RP4 is preferably used for these purposes. *E. coli* vectors which carry a 1.9 kb fragment ("mob" site) of RP4 can be used with advantage in the method of the invention.

Suitable mobilizer strains include modified *E. coli* strains which contain a plasmid in the chromosome, that is, in integrated form, or present in nonintegrated form and capable of making available the functions necessary for mobilization.

Strains that are especially suitable for use in the present invention are those in which an RP4 derivative is integrated into the chromosome and whose transfer function acts in trans on the "mob" site of the above-named vectors.

Suitable vectors and *E. coli* mobilizer strains are known from U.S. Pat. No. 4,626,504 and are deposited in the Northern Regional Research Center:

TABLE 1

| Strains | NRRL deposit No. |
| --- | --- |
| E. coli CSH52/pSUP101 | B-15484 |
| E. coli CSH52/pSUP201 | B-15487 |
| E. coli CSH52/pSUP202 | B-15488 |
| E. coli CSH52/pSUP203 | B-15489 |
| E. coli CSH52/pSUP301 | B-15492 |
| E. coli CSH52/pSUP401 | B-15494 |
| E. coli SM10 | B-15481 |
| E. coli S68-7 | B-15482 |
| E. coli S17-1 | B-15483 |

Other vectors, such as pSUP102 or pSUP205, are known from the literature and are obtained according to analogous methods from known vectors (Simon et al., Methods of Enzymology 118 640 fl. (1986) and Biotechnology, November, 1983).

The restriction defect can be genetically based and produced, for example, by means of mutagenic agents (e.g. NTG: methylnitronitrosoguanidine); however, it can also be physiologically based and produced, for example, by means of a heat shock. Heat treatment of the recipient immediately before crossing has proven to be especially effective. Intact or spheroplastized cells are to be used.

Heat shock for a duration of 1 to 30 min., preferably approximately 9 min., at 45° to 55° C., preferably approximately 49° C., makes it possible to solve the problem to which the invention is directed, increasing the transfer frequency.

Vectors such as those cited in Table 1 can be viewed as suicide vectors since, after the transfer into gram-positive bacteria strains, they are no longer able to replicate. They are suitable, however, for the insertion mutagenesis of gram-positive bacteria strains. A cloned sequence, for example, a gene fragment coding for a protein having enzyme activity in a gram-positive bacteria strain, can be inserted into one of the mobilizable vectors and that vector can be used in accordance with the invention (using known methods where appropriate). The resulting vector can be transferred, by conjugation, from an *E. coli* mobilizer strain into a gram-positive strain in which homologous recombination with the corresponding intact gene located there can take place. The homologous recombination results either in the insertion of the entire resulting vector (single cross-over) or in an exchange of the introduced gene fragment with the homologous sequence in the intact gene of the recipient (double cross-over).

The method of the invention is also carried out with mobilizable, non-self-transferrable vectors which comprise:

a) a DNA segment containing a replicon which can function in *E. coli;* b) a second DNA segment containing the DNA fragments coding for the mobilization function and the transfer function ("mob" site and oriT);

c) a third DNA segment which recombines homologously in gram-positive bacteria and/or contains a replicon which is functional in gram-positive bacteria; and d) optionally, a transposon instead of (c) above or contained in (c) above.

The above also constitutes subject matter of the invention. Preferred vectors are those in which the third DNA segment (c) is derived from a vector which replicates in Coryneform bacteria, especially *Corynebacterium glutamicum*.

One vector of the invention is pECM1 (DSM 4982), which was deposited in the German Collection for Microorganisms (DSM) in accordance with the Budapest Convention. In this connection, the expression "vector" used herein designates a plasmid vector, phage vector or plasmid, according to the origin of the element to be designated.

The localization and diminution of replicons as a basis of vector development for gram-positive bacteria is simplified. The crossing protocol permits the conjugative transfer of mobilizable shuttle vectors from an *E. coli* mobilizer strain into gram positive bacteria having an intact cell wall or spheroplastized gram-positive bacteria, with a frequency of approximately $10^{-1}$ to $10^{-3}$, relative to the donor titer.

The transfer of the vectors can be checked by means of characteristic antibiotic resistance markers as well as by lysis of the transconjugants with subsequent analysis of the plasmid content by agarose gel electrophoresis. A change of the vectors as a result of the conjugation process is not observed. Natural transformation as transfer mechanism can be excluded by monitoring the crossed.

The high transfer achieved by means of conjugative transfer will make possible, in the future, the use of transposons even in gram-positive bacteria, for which a natural transformation system has not previously been demonstrated.

Other preferred vectors are those in which the DNA segments (a) and (b) above are derived from one of the vectors from the group pSUP101, pSUP201, pSUP202, pSUP203, pSUP205, pSUP301 and pSUP401.

Figure 1:
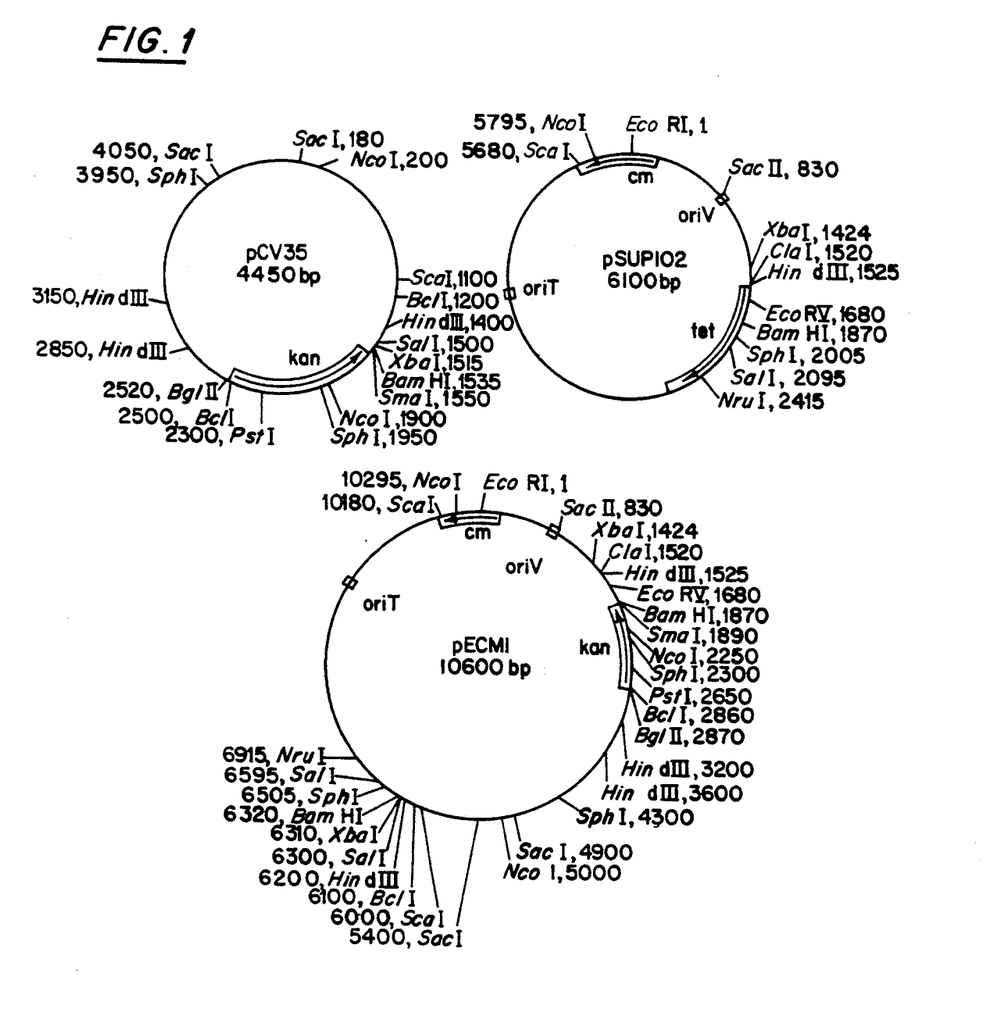
Figure 2:
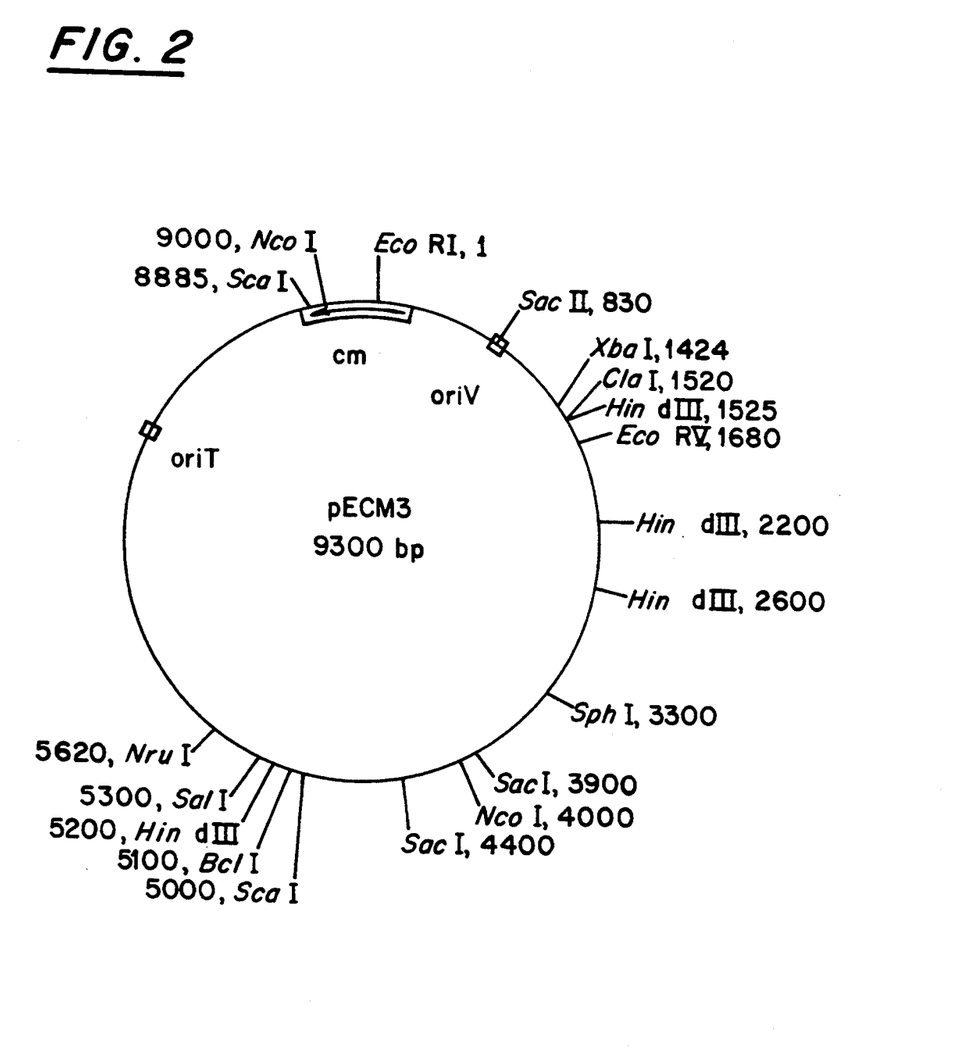

Vectors which exhibit preferred features are pECM1 and pECM3, the restriction maps of which are shown in FIGS. 1 and 2.

The host range of these vectors comprises the amino-acid-secreting strains of the genera Corynebacterium and Brevibacterium, especially

*Corynebacterium acetoacidophilum*
*Corynebacterium alutamicum*
*Corynebacterium glutamicum* ATCC 13032
*Corynebacterium glutamicum* ATCC 13058
*Corynebacterium hydrocarboclastum*
*Corynebacterium ilicis*
*Corynebacterium lilium*
*Corynebacterium sp.* DSM 20140
*Brevibacterium flavum*
*Brevibacterium lactofermentum*
*Brevibacterium lyticum*
*Brevibacterium roseum*
*Micrococcus sodonense*

The method of the invention for conjugative transfer also makes possible a rapid determination of the host range of replicons, especially of known plasmids such as, for example, pHM1519.

The present invention is described in greater detail in the following non-limiting Examples.

EXAMPLE 1

Construction of a Mobilizable Shuttle Vector

The mobilizable shuttle vector pECM1 (FIG. 1) was constructed by fusion of the mobilizable E coli vector pSUP102 (FIG. 1; Simon et al. Methods in Enzymol. 118:641–658 (1986)) with the Corynebacterium glutamicum plasmid pCV34 (FIG. 1).

0.5 μg pSUP102 DNA and 1 μg pCV35 DNA are incubated in a React 3 restriction buffer (producer: BRL-Gibco, Karlsruhe) in the presence of 1 μl BamHI restriction enzyme (BRL-Gibco, Karlsruhe) each for 1 h at 37° C.

Completely cut pSUP102 DNA is compounded in the restriction buffer with linearized pCV35 DNA and the mixture incubated for 5 min. at 70° C. The conditions for the ligation are adjusted with the aid of the ligation buffer (BRL-Gibco) and ATP. The mixture is ligated in the presence of 1 μl T4 DNA ligase for 16 h at 14° C.

The ligation mixture is introduced by transformation (according to Maniatis et al. Molecular Cloning, Cold Spring Harbor Publications (1982)) into cells of the strain E. coli S17-1, which are capable of taking up plasmid DNA upon treatment with $CaCl_2$.

Cells which receive pECM1 become resistent to the antibiotics kanamycin and chloramphenicol (50 μg/ml) but are sensitive to tetracycline (5 μg/ml).

pECM1 replicates in E. coli and in C. glutamicum and can be mobilized with the aid of the transfer functions of the RP4 derivative integrated in the chromosome of the mobilizer strain E. coli S17-1.

pECM1 has been deposited in E. coli S17-1 in the German Collection for Microorganisms under No. DSM 4982.

Mutagenesis of the BglII cleavage site of pCV34 and production of plasmid pCV35

Plasmid pCV34, deposited as DSM 5025, was isolated according to Thierbach et al. (Appl. Microbiol. Biotechnol. 29:356–362 (1988)) and cut with the enzyme BglII. The mutagenesis reaction mix consisted of approximately 2 μg plasmid DNA in 60 μl TE buffer, 180 μl 1.5M hydroxylamine-HCl in 25 M EDTA, 5 μl 0.25M EDTA and 13 μl 1M Tris-HCl, pH 8.0. The reaction was mixed and incubated 20 minutes at 60° C. After phenol treatment and ethanol precipitation of the plasmid DNA (Manjarls et al. Molecular Cloning, Cold Spring Harbor Publications (1982)), the DNA pellet was taken up in 20 μl TE and treated with T4 DNA ligase. After transformation of C. glutamicum ATCC 13032 with the plasmid DNA, transformants were able to be isolated in which one of the two BglII cleavage sites had been lost. pCV34 is new and exhibits the same kanamycin resistance level as pCV33 (see parallel application DE-38 41454).

Construction of shuttle vector pECM3 pECM3 (FIG. 2) is produced from pECM1 by deletion of a 0.3 kb SalI fragment and of a BamHI/BglII fragment which carries the information for the kanamycin resistance.

The construction of this vector takes place in accordance with generally known methods from the deposited vector pECM1.

EXAMPLE 2

Detailed Crossing Protocol

For simplicity, the invention is further described by reference to the mobilization of shuttle vector pECM1 from E. coli S17-1 to C. glutamicum ATCC 13032. However, when appropriate replicons are used, transfer to other microorganisms can also be effected (see also in this regard Example 3).

The following crossing protocol is used for a conjugative transfer of pECM1 from E. coli S17-1 into C. glutamicum ATCC 13032 cells having intact cell walls:

10 ml Luria broth medium with 50 μg/ml kanamycin are inoculated in a test tube with cells of mobilizer strain E. coli S17-1 carrying pECM1 and incubated overnight at 37° C. in a roller (initial donor culture).

For the cultivation of the recipient, 10 ml Luria broth-glucose medium (with 50 μg/ml nalidixic acid) per crossing reaction mixture are placed in a test tube with C. glutamicum ATCC 13032 and incubated at 30° C. in a roller until an optical density of 3–4 at a wavelength of 580 nm has been reached (approximately 20 h).

For the crossing, 10 ml Luria broth medium (with 50 μg/ml kanamycin) are placed (per reaction) in a test tube with 100 μl of the initial donor culture and incubated at 37° C. in a roller until an optical density (at 580 nm) of 0.6–0.7 has been reached.

The recipient cultures, in a test tube, are placed for 13 min. in a water bath at a temperature of 49° C. (heat shock). The heat-treated recipient cultures are transferred into sterile PE tubes and are pelleted by centrifuging for 8 min. at 3000 rpms. The supernatant is discarded and the pellet resuspended.

Donor and recipient cells are used in a ratio of 1:5 for the crossing. An appropriate amount of donor culture is transferred into sterile PE tubes and centrifuged for 8 min. at 3000 rpms. The supernatant is discarded. Then, the resuspended recipient cells are pipetted onto the donor cell pellet. The suspension is centrifuged again for 8 min. at 3000 rpms and the supernatant reduced to a maximum of 500 μl. The cells are very carefully resuspended and dropped onto cellulose acetate filters (0.45 μm pore size) which had been placed on plates containing Luria broth-glucose medium with agar.

The plates are incubated 18 h at 30° C. and the filters subsequently elutriated with 0.8 ml Luria broth medium. The selection of the transconjugants takes place at 30° C. on Luria broth-glucose medium with agar containing kanamycin (25 μg/ml) and nalidixic acid (50 μm/ml).

If the conjugative transfer of pECM1 into spheroplastized recipient cells is to take place, then the following modifications are to be observed:

The spheroplast reaction mix (approximately 330 μl) is suspended before the heat treatment is carried out in 10 ml TSMC* buffer and incubated for at least 3 h at 30° C.

Recipient cells and crossing mixture are not resuspended after centrifugation in Luria broth medium but rather in TSMC* buffer.

The selection of the transconjugants takes place on osmotically stabilized sorbitol (SB) regeneration plates containing kanamycin (17.5 μg/ml) and nalidixic acid (50 μg/ml).

Conjugative transfer of the mobilizable shuttle vector pECM1 from E. coli S17-1 to Corynebacterium glutamicum ATCC 13032.

The mobilizable shuttle vector pECM1 (Example 1) is mobilized, in accordance with the previously described crossing protocol, from E. coli S17-1 to C. glutamicum.

Both spheroplastized as well as C. glutamicum cells having intact cell walls are used as recipients. In addition, a C. glutamicum mutant is used whose restriction system has been eliminated by mutagenesis with NTG (res⁻ mutant*).

The following frequencies result for the transfer of pECM1 by conjugation:

| Recipient | non-spheropl. res⁺-cells | spheropl. res⁺-cells | non-spheropl. res⁻-cells |
|---|---|---|---|
| without heat shock | $5 \times 10^{-7}$ | $3 \times 10^{-7}$ | $2 \times 10^{-2}$ |
| with heat shock | $1 \times 10^{-2}$ | $4 \times 10^{-3}$ | $9 \times 10^{-3}$ |

The frequencies determined are average values of three crossings carried out independently of each other and refer in each instance to the donor titer.

The example cited here clearly shows that a limited-time heat treatment (13 min., 49° C.) interferes with the restriction system of the recipient cells and results in transfer frequencies elevated by a factor of $10^4$–$10^5$.

An efficient transfer of pECM1, with the aid of heat shock, is possible both into intact cell wall and also into spheroplastized C. glutamicum cells. The slight difference in the transfer frequencies observed results from a tendency of the spheroplastized cells to lysis which is increased by the damaging of the cell wall.

The transfer frequencies achieved during the use of heat-treated recipients are achieved in the absence of heat treatment only when a restriction-defective mutant (res⁻ mutant*) of C. glutamicum is used.

EXAMPLE 3

Conjugative transfer of pECM1 into Coryneform bacteria—Determination of the host range of pHM1519.

pHM1519 is a 3 kb cryptic plasmid which was isolated from C. glutamicum ATCC 13058 (Miwa et al. Agric. Biol. Chem. 48:2901-2903 (1984)).

pHM1519 is the base replicon of the C. glutamicum vector pCV35, which was used for the construction of the mobilizable E. coli—C. glutamicum shuttle vector pECM1 (Example 1).

To determine host range, pECM1 is mobilized from E. coli S17-1 into representatives of the group of Coryneform bacteria.

The crossings are carried out according to the previously described protocol. The selection of the transconjugants takes place on LBKm₂₅Nx₅₀ medium and the natural resistance to the antibiotic nalidixic acid, which resistance is found throughout Coryneform bacteria, is utilized for selecting against the donor.

The transfer of pECM1 is confirmed by means of the resistances to the antibiotics kanamycin and chloramphenicol imparted by the vector as well as by lysis of the transconjugants (modified according to Birnboim et al. Nucl. Acids. Res. 7:1513-1523) and subsequent analysis of the plasmid content by means of agarose gel electrophoresis.

The result of this experiment shows that the host range of pHM1519 comprises a number of representatives from the group of Coryneform bacteria which are in part of considerable commercial interest:
Corynebacterium acetoacidophilum
Corynebacterium glutamicum ATCC 13032
Corynebacterium glutamicum ATCC 13058
Corynebacterium hydrocarboclastum
Corynebacterium ilicis
Corynebacterium lilium
Corynebacterium sp. DSM 20140
Brevibacterium divaricatum
Brevibacterium flavum
Brevibacterium lactofermentum
Brevibacterium lyticum
Brevibacterium roseum
Brevibacterium stationis
Micrococcus sodonense
Corynebacterium callunae DSM 20147
Corynebacterium pilosum DSM 20521
Corynebacterium fascians DSM 20131
Corynebacterium herculis DSM 20310
Corynebacterium melassecola ATCC 17965
Corynebacterium melassecola ATCC 17966
Arthrobacter albidus DSM 20128
Brevibacterium ammoniagenes 20305

Similar tests showed that the following strains do not belong to the host range of the pHM1519 replicon:
Clavibacter michiganenense
Clavibacter nebraskense
Corynebacterium flaccumfaciens
Bacillus subtilis
Brevibacterium linens
Brevibacterium ketoglutamicum
Brevibacterium pusillum
Brevibacterium testaceum

EXAMPLE 4

Insertion mutagenesis of C. glutamicum using the example of the lysA gene

The lysA gene codes for the enzyme mesodiaminopimelate decarboxylase, which catalyses the last step in the biosynthesis of lysine. After complementation of the E. coli lysA mutant W7 (Wientjes et al. J. Bacteriol. 164:331-337 (1985)) with a gene bank of C. glutamicum ATCC 13032 in the E. coli vector pUC18, which gene bank is described in European patent application 89114632.6, the hybrid plasmid pTG1225 was isolated, which carries a 5.8 kb insertion of ATCC 13032 DNA.

Figure 3:
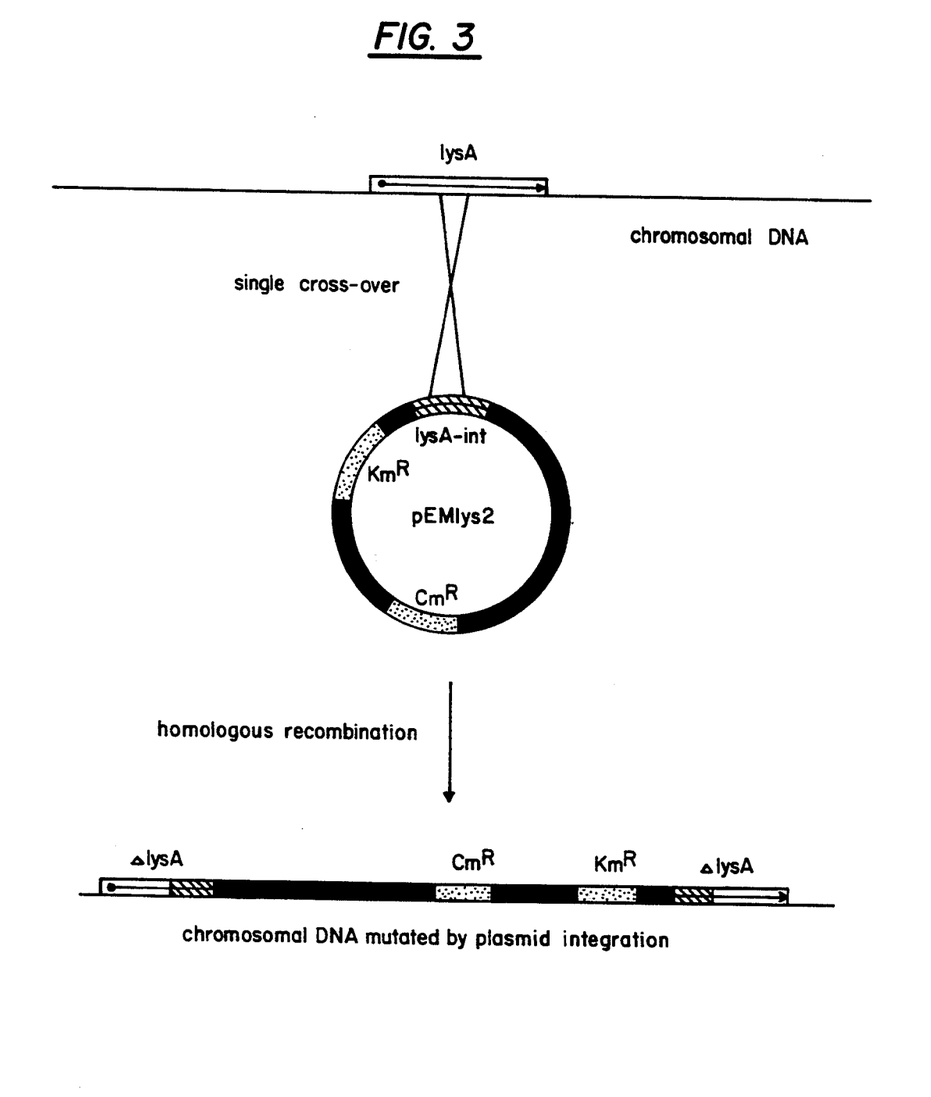

A 1 kb BclI-SalI fragment of the plasmid pTG1225 was selected based on the published sequence of the lysA gene of C. glutamicum (Yeh et al. Mol. Gen. Genet. 212:112-119 (1988)), which fragment carries an internal region of the lysA coding region. Upon homologous recombination into the chromosome, the chromosomal gene is inactivated by integration of the vector (FIG. 3).

The mobilizable, non-self-transmissible vector pEMlys2 was constructed for mutagenesis by integration. This vector comprises
a) the plasmid pSUP102 (Simon et al. Methods in Enymology 118:641-658), which carries a replicon functional in E. coli and carries the "mob" region;
b) an internal fragment of the lysA gene from C. glutamicum, and
c) the kanamycin resistance determinant of transposon Tn903 selectable in C. glutamicum (Veira & Messing Gene 19:259-268 (1982)).

Figure 4:
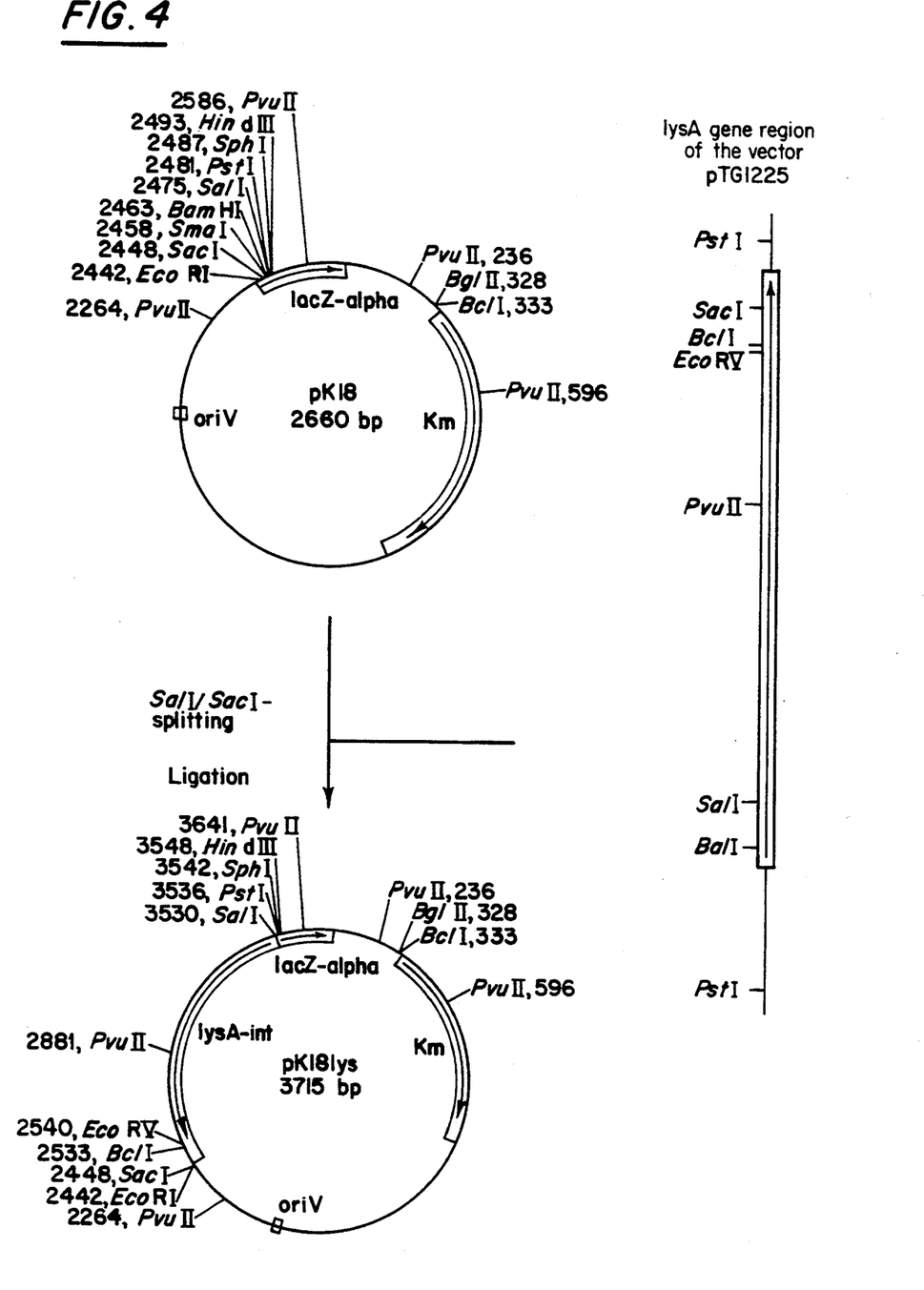
Figure 5:
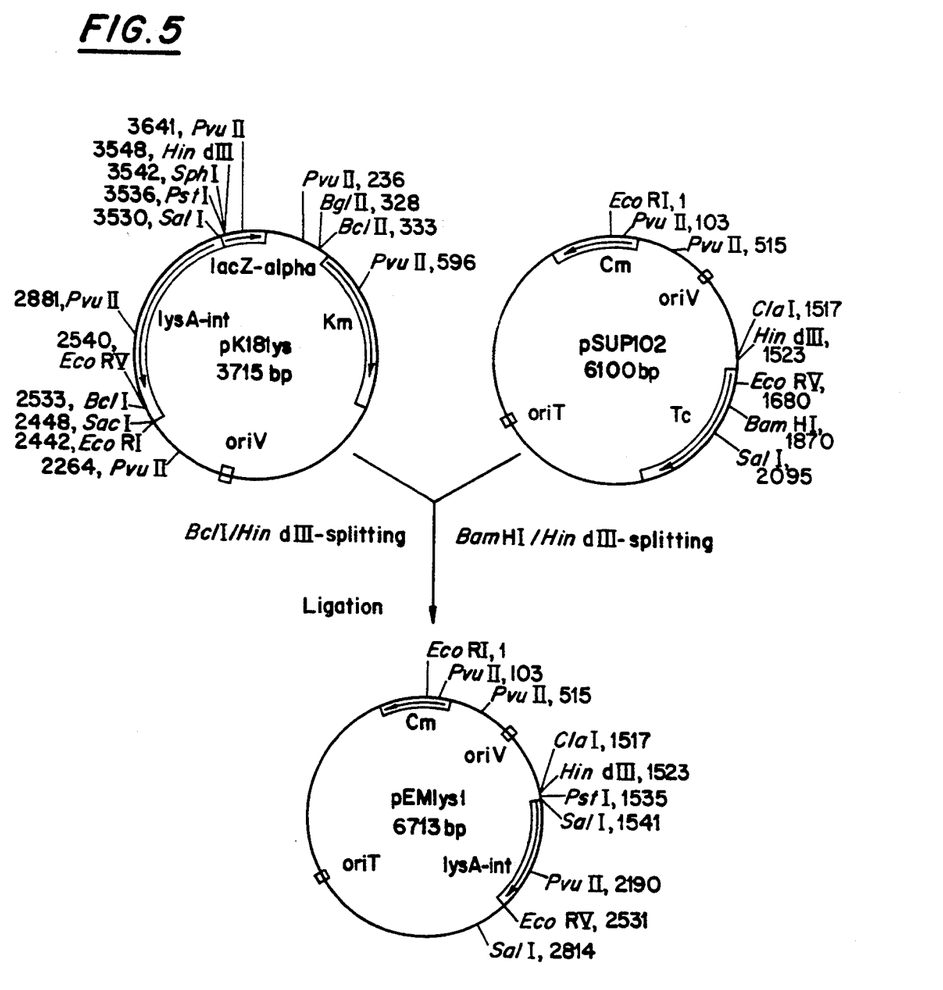
FIG. 5: Construction of the vector pEMlys1.
Legend: (see foregoing Legends for explanation of abbreviations)
Figure 6:
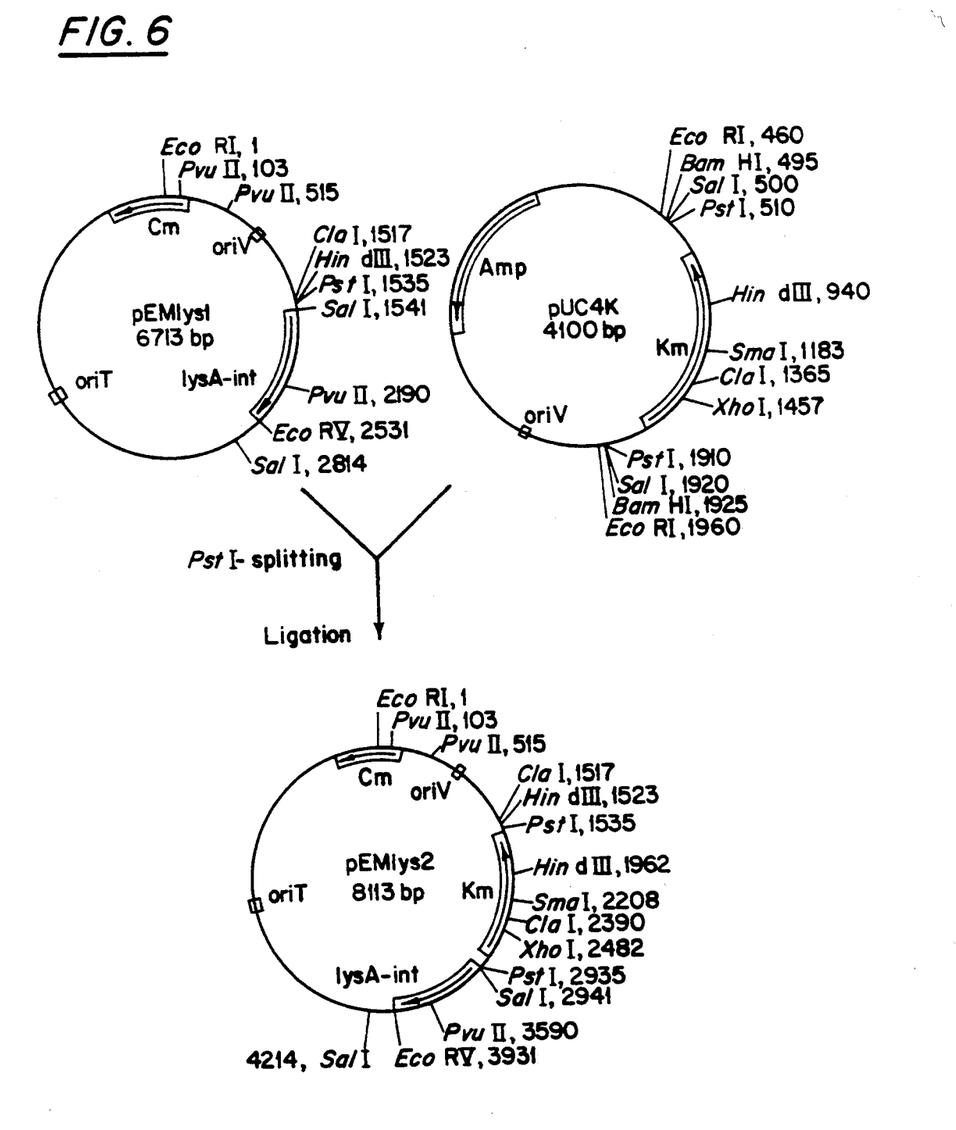
FIG. 6: Construction of the vector pEMlys2.
Legend: (see foregoing Legends for explanation of abbreviations)

The construction of the vector pEMlys2 (FIGS. 4–6) took place according to the known methods of recombinant DNA technology.

An internal fragment of the lysA gene (1.1 kb) was cut out of plasmid pTG1225 by means of the restriction enzymes SalI and SacI and ligated with the vector pK18 which was likewise cut (Pridmore Gene 56:309-312 (1987)).

An internal fragment of the lysA coding region was isolated from the resulting plasmid pK18lys (3.7 kb) by means of cutting with the restriction enzymes BclI and HindIII and fused with the BamHI and HindIII-restricted vector pSUP102.

The kanamycin resistance gene of transposon Tn903 was cloned into the resulting vector pEMlys1 (6.7 kb). To this end, pEMlys1 was linearized by digestion with PstI and ligated with a 1.4 kb PstI fragment of vector pUC4K.

The vector pEMlys2 (8.1 kb) produced in this manner was transformed into the mobilizer strain E. coli S 17-1. The conjugative transfer of this plasmid from E. coli to C. glutamicum ATCC 13032 took place according to the protocol presented in detail in Example 2.

Kanamycin-resistant colonies occurred with a frequency of $2 \times 10^{-7}$ relative to the donor titer.

The kanamycin-resistant transconjugants were screened on minimum agar (Kaneko & Sakaguchi Agric, Biol. Chem. 43:1007-1013 (1979)) and on minimum agar supplemented with L-lysine. The transconjugants investigated in this manner exhibited a lysine-auxotrophic phenotype in accordance with the insertion inactivation of the chromosomal lysA gene due to the integration of pEMlys2.

On lysis of the transconjugants, carried out according to Birnboim etal. (Nucl. Acids. Res. 7:1513-1523) followed by analysis of the plasmid content by agarose gel electrophoresis, no free plasmids were found in the cells.

Proof of the specific integration was provided by digoxygenine hybridization (Khandjian, Bio/Technology 5:165 (1987)) of the labelled E. coli vector pSUP102 to total DNA isolated from C. glutamicum wild-type cells and the transconjugants; only DNA from transconjugants with the DNA of the E. coli vector hybridized.

The entire contents of all references cited hereinabove are hereby incorporated by reference.

While the present invention has been described in some detail for purposes of clarity and understanding, one skilled in the art will appreciate that various changes can be made in form and detail without departing from the true scope of the invention.

What is claimed is:

1. A method for the conjugative transfer of a mobilizable vector from cells of an E. coli mobilizer strain to Coryneform bacterial cells which comprising producing restriction-defective cells of said Coryneform bacteria and crossing said defective cells with cells of said E. coli strain carrying said vector under conditions such that transfer of said vector to said defective cells is effected.

2. The method according to claim 1, wherein said vector comprises a mob site DNA segment and said E. coli mobilizer strain contains a plasmid that codes for a Mob-site that effects mobilization of said vector.

3. The method according to claim 2 wherein said plasmid is present as an extrachromosomal element.

4. The method according to claim 2, wherein mob site is a 1.9 kb DNA segment of the plasmid RP4, an RP4 derivative being transferably by conjugation in the presence of a transfer function encoded by a gene that acts in trans, integrated into the chromosome of said E. coli mobilizer strain.

5. The method according to claim 1, wherein said E. coli mobilizer strain is selected from the group consisting of E. coli S17-1, E. coli SM10, and E. coli S68-7.

6. The method according to claim 1, wherein said vector is selected from the group consisting of pSUP101, pSUP102, pSUP201, pSUP202, pSUP203, pSUP205, pSUP301 and pSUP401.

7. The method according to claim 1, wherein said defective cells of said Coryneform bacteria are produced by heat shocking said Coryneform bacteria prior to said crossing step.

8. The method according to claim 1, wherein said defective cells are intact bret res cells.

9. The method according to claim 1, wherein said defective cells are spheroplastized cells.

10. The method according to claim 1, wherein said mobilizable vector comprises a gene, or fragment thereof, active in said Coryneform bacteria, which gene undergoes homologous recombination when transferred into said Coryneform bacteria.

11. The method according to claim 1, wherein said mobilizable vector comprises a Procaryotic transposon.

12. The method according to claim 1, wherein said mobilizable vector comprises a shuttle vector fused with a plasmid or vector which replicates in said Coryneform bacteria.

13. A mobilizable, non-self-transferrable vector, comprising:
 i) a first DNA segment containing a replicon functional in E. coli;
 ii) a second DNA segment containing DNA sequences coding for mobilization (mob site) and transfer (oriT); and
 iii) a third DNA segment that recombines homologously in Coryneform bacteria or that contains a replicon functional in Coryneform bacteria.

14. The vector according to claim 13, wherein said third DNA segment further comprises a Procaryotic transposon.

15. The vector according to claim 13, wherein said third DNA segment is derived from a vector that replicates in Coryneform bacteria.

16. The vector according to claim 15, wherein said third DNA segment is derived from the vector pCV35.

17. The vector according to claim 13, wherein said first and second DNA segments are derived from a vector selected from the group consisting of pSUP101, pSUP102, pSUP201, pSUP202, pSUP203, pSUP205, pSUP301 and pSUP401.

18. A mobilizable, non-self-transferrable vector comprising:
 i) a first DNA segment containing a replicon functional in E. coli;
 ii) a second DNA segment containing DNA sequences coding for mobilization (mob site) and transfer (oriT); and
 iii) a Procaryotic transposon.

19. A vector pECM1, accession number DSM 4982.

20. A vector pECM3 having the restriction map shown in FIG. 2.

* * * * *